(12) United States Patent
Hyde-Edwards et al.

(10) Patent No.: US 8,686,214 B2
(45) Date of Patent: Apr. 1, 2014

(54) POST-NIPPLE RECONSTRUCTION PROTECTOR

(75) Inventors: Julie Hyde-Edwards, Royal Oak, MI (US); Miguel A. Linares, Bloomfield Hills, MI (US)

(73) Assignee: Julie Hyde-Edwards, Royal Oak, MI (US)

( * ) Notice: Subject to any disclaimer, the term of this patent is extended or adjusted under 35 U.S.C. 154(b) by 37 days.

(21) Appl. No.: 12/869,809

(22) Filed: Aug. 27, 2010

(65) Prior Publication Data
US 2011/0054374 A1 Mar. 3, 2011

Related U.S. Application Data

(60) Provisional application No. 61/237,383, filed on Aug. 27, 2009.

(51) Int. Cl.
*A61F 13/00* (2006.01)
*A61J 13/00* (2006.01)

(52) U.S. Cl.
USPC .................. 602/54; 602/41; 602/43; 602/60; 602/61; 128/888; 128/890

(58) Field of Classification Search
USPC ...................... 602/41–43, 47, 52–55, 58–61; 128/888–890; 450/39, 54–57, 60, 61, 450/81
See application file for complete search history.

(56) References Cited

U.S. PATENT DOCUMENTS

| | | | |
|---|---|---|---|
| 4,754,750 A | 7/1988 | Imonti | |
| 4,790,309 A | 12/1988 | Becker | |
| 4,870,977 A | 10/1989 | Imonti | |
| 5,032,103 A * | 7/1991 | Larsson | 450/37 |
| 5,522,892 A * | 6/1996 | Lin | 623/7 |
| 5,998,693 A | 12/1999 | Zagame | |
| 6,200,195 B1 | 3/2001 | Furuno et al. | |
| 7,152,606 B1 * | 12/2006 | Schindler | 128/889 |
| 2006/0106329 A1 | 5/2006 | Hammer et al. | |
| 2008/0188787 A1 * | 8/2008 | Clark | 602/61 |
| 2009/0149114 A1 | 6/2009 | Horton et al. | |

* cited by examiner

*Primary Examiner* — Patricia Bianco
*Assistant Examiner* — Keri J Nelson
(74) *Attorney, Agent, or Firm* — Gifford, Krass, Sprinkle, Anderson & Citkowski, P.C.

(57) ABSTRACT

An improved post-operative dressing for providing both breast and, notably, nipple reconstruction and which in particular establishes custom lateral supporting of the nipple annulus. A body is constructed of a medical grade silicone and exhibits a three dimensional shape adapted for placement over the reconstructed breast and an aperture defined by an inner rim configured within the body is adapted to seat therethrough an associated nipple graft in a laterally supporting and non-pressure applied fashion. A number of secondary advantages incorporated into the body include each of apertures for breathability, suction/adherence properties, and impregnation or entrainment within the body inner surface of any form of anti-infection medicine.

4 Claims, 6 Drawing Sheets

FIG. 4A
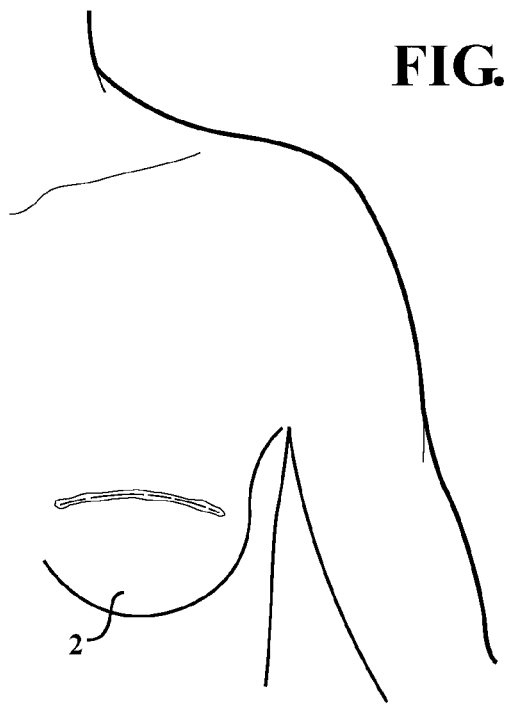
FIG. 4B
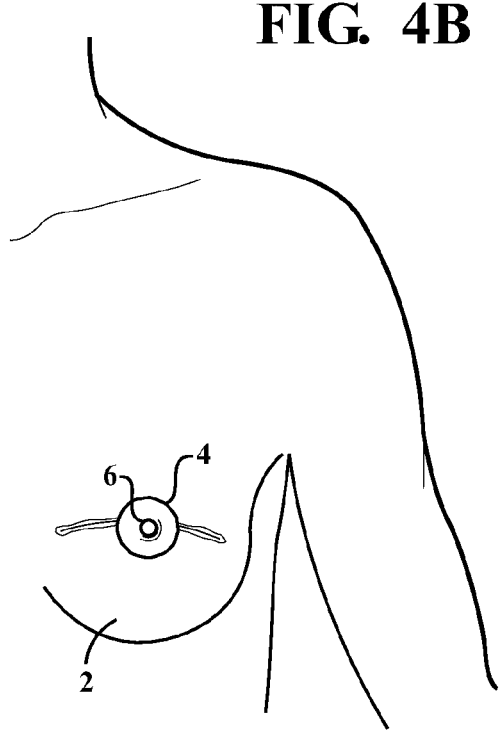
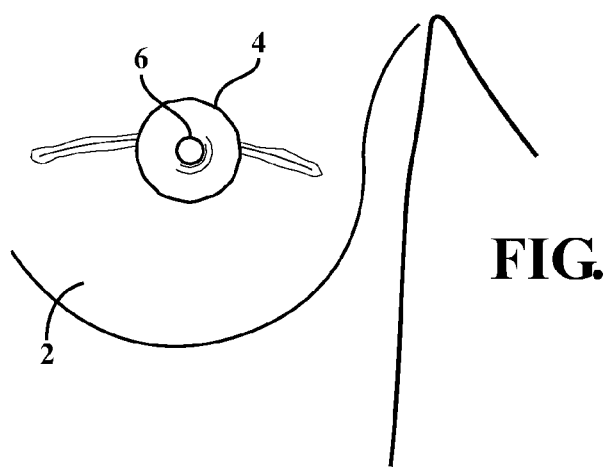
FIG. 4C

POST-NIPPLE RECONSTRUCTION PROTECTOR

CROSS-REFERENCE TO RELATED APPLICATIONS

This Application claims the benefit of U.S. Provisional Application 61/237,383 filed on Aug. 27, 2009.

FIELD OF THE INVENTION

The present invention discloses a one-piece silicone gel dressing for post operative use in breast and nipple reconstruction surgeries, and exhibiting a generally arcuate and variable thickness consistency and which is generally shaped to correspond to the contour of the female breast mound. More specifically, the present invention teaches such a device in which a center cutout and aperture defined portion, in combination with the concave surface of the device, provides a desired minor degree of gentle pressure to the surrounding areola, while concurrently providing lateral support but no direct pressure to the reconstructed nipple and which is permitted to project through the center aperture.

BACKGROUND OF THE INVENTION

The prior art is documented with examples of breast reconstruction devices, such as following mastectomy or other breast related surgeries and which are typically geared toward shaping of the breast. A shortcoming of such prior art devices is in the shaping of the reconstructed nipple, with such known applications including clips, collar devices and the like which typically attach directly to the areola, in surrounding fashion to a reconstructed nipple graft. Shortcomings include both discomfort to the wearer, as well as the evident nature of the device when worn under clothing.

An example of one known nipple reconstruction device is set forth in US Patent Application Publication No. 2006/0106329, to Hammer et al., and which including a padded component 12, a core component 14 and an attaching component 16. In relevant part, the core 14 contains a hollow opening 18 for permitting insertion of the reconstructed nipple, however establishes no lateral supporting or other reconstructive aspects not related to the underlying breast mound.

Imonti, U.S. Pat. No. 4,870,977 teaches a surgical protector for raised wounds and which includes an aereola/nipple surface wound protector exhibiting a cone shape. Becker, U.S. Pat. No. 4,790,309 discloses a tissue expander stent for nipple reconstruction and which defines a frusto-conical shaped segment with a short cylindrical tubular element extending outwardly and which encompasses a rigid ring. In application, the conical segment is forced downwardly onto the breast, following which the nipple is sutured to the stent in order that the resiliency of the conical segment maintains the sutures under tension and tends to pull the nipple upwardly during healing.

SUMMARY OF THE INVENTION

The present invention discloses an improved post-operative dressing for providing both breast and, notably, nipple reconstruction which is an improvement over the prior art and which in particular establishes custom lateral supporting of the nipple annulus, combined with a series of secondary advantages including, most notably, invisibility when worn under clothing and, alternatively or accumulatively, each of breathability, suction/adherence, and impregnation or entrainment of any form of anti-biotic (anti-infection) medicine. The body is constructed of a medical grade silicone and exhibits a three dimensional shape adapted for placement over the reconstructed breast and an aperture defined by an inner rim configured within the body is adapted to seat therethrough an associated nipple graft in a laterally supporting and non-pressure applied fashion.

In one non-limiting variant, the outer perimeter of the body is selected from any of including a rounded, oval or ellipsoidal shape and further such that the body exhibits a narrow most and tapered outer profile increasing in dimension to a most thickened interior corresponding to location of the aperture defining inner rim. A tacky adhesive may be applied to an inner concave surface associated with the body to enhance surface gripping onto the surrounding skin. Other features include the adhesive exhibited by a gentle paper tape.

Additional features include a gripping pattern formed into an outer radial edge portion of an inner concave surface of the body and providing additional gripping support against the wearer's skin and about the outer perimeter of the dressing. Pluralities of surface perforations are formed through the body and accessible to a surface in order to improve air permeability. Additionally, the body may include interior molded channels communicating interior located apertures with the wearer's skin, with outer located baffles permitting fresh air to pass through the dressing body to the breast and for generated body warmth to escape through the baffles.

BRIEF DESCRIPTION OF THE DRAWINGS

Reference will now be made to the attached drawing, when read in combination with the following detailed description, wherein like reference numerals refer to like parts throughout the several views, and in which:

FIGS. 4A-4G are a progression of views detailing a breast and nipple reconstruction, followed by post surgical application of the post nipple reconstruction dressing/scar reduction and nipple protector device according to the present invention and further showing the variable thickness of the dressing device including a greatest thickness at a center location corresponding to the reconstructed nipple seating through the center aperture;

DETAILED DESCRIPTION OF THE PREFERRED EMBODIMENTS

With reference to the several illustrations described below, the present invention discloses a one-piece, three dimensional shaped and medical grade silicone gel dressing 10 for post operative use in breast/nipple reconstruction surgeries. As will be described in more detail, the dressing provides a number of improvements not evident in the prior art, including notably provision of a suitable one piece dressing for providing reconstructed breast support in combination with being properly sized for laterally supporting (but not pinching or deforming) the sensitive reconstructed nipple, such dressing further capable of being worn in a virtually invisible nature underneath any normal feminine garment.

Figure 1:
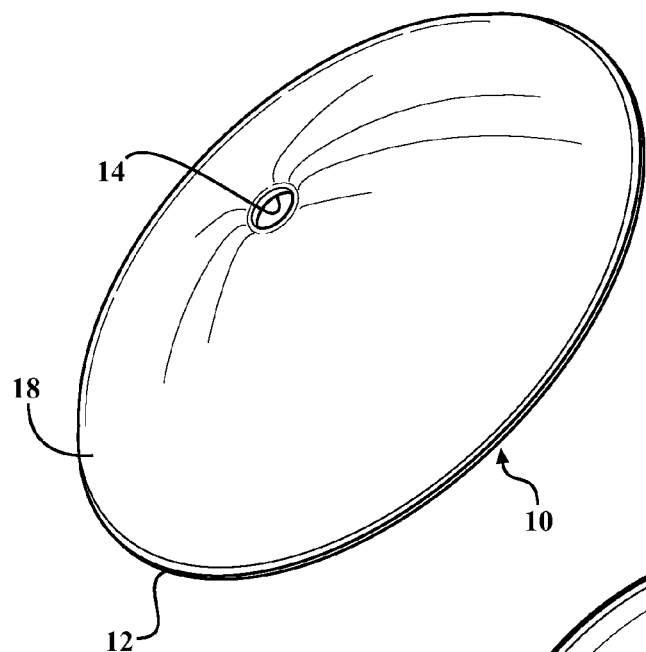
FIG. 1 is a perspective view of the dressing device according to one potential embodiment of the present invention.
Figure 2:
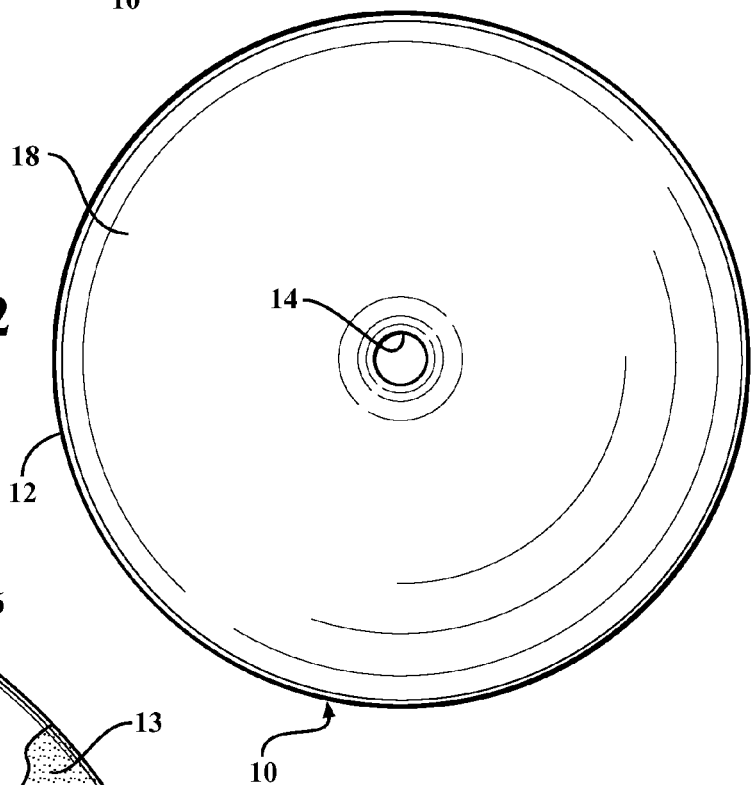
FIG. 2 is a top view of the device shown in FIG. 1.

With reference initially to FIG. 1, the dressing is provided as a body 10, again typically constructed of a medical grade silicone but also contemplating the inclusion of other suitable materials. The body exhibits a generally arcuate and variable thickness consistency and which is generally shaped to correspond to the contour of the female breast mound. As shown, the device 10 exhibits a generally tapered and narrowest thickness associated with its outermost and perimeter defined edge, at 12, and which can adopt any of a generally round, oval or ellipsoidal shape depending upon the overall contour of the reconstructed breast to which it is applied.

As further shown in FIGS. 4A-4F is a progression of views detailing a breast and nipple reconstruction, followed by post surgical application of the post nipple reconstruction dressing/scar reduction and nipple protector device according to the present invention and further showing the variable thickness of the dressing device including a greatest thickness at a center location corresponding to the reconstructed nipple seating through the center aperture. The thickness of the device increases to a maximum dimension (such as ½" in one desired variant) at a generally central location corresponding further to an aperture (see inner annular rim 14 in each of FIGS. 4D-4F).

As is known, and following a mastectomy procedure (see again FIGS. 4A-4C), a complete breast reconstruction includes recreating the breast mound 2, the nipple 6 and areola complex (NAC) 4, such that the breasts are symmetric with regard to pigmentation, shape, size, projection and position. This is a multi-stage process, with the NAC reconstruction often considered to be the final stage.

The center cutout and aperture defined rim 14, in combination with the overall (inner facing) concave surface of the device (see further at 16 in FIG. 4E), is custom designed in order to provide adequate lateral supporting aspect around the entire periphery of the reconstructed nipple, this further defined as a desired minor degree of gentle pressure when applied to a breast 2, specifically to a surrounding areola 4 associated with a central projecting reconstructed nipple 6 which comfortably seats through the central aperture and is gently and laterally supported by its rim 14).

Figure 3:
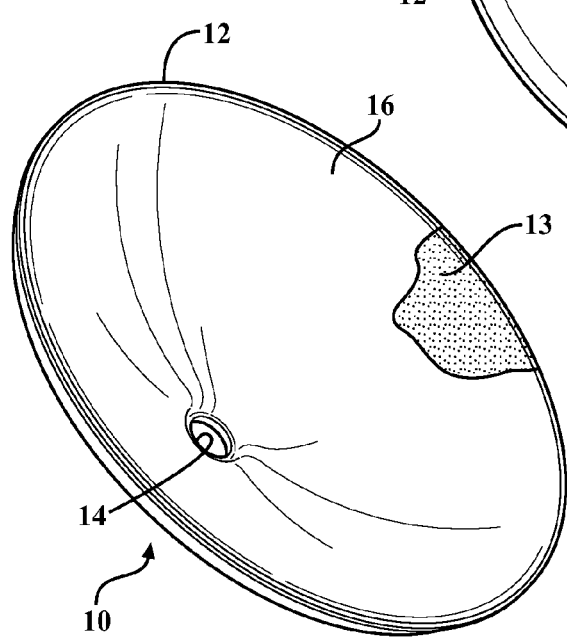
FIG. 3 is an inverted bottom or inside view of the device.

In this fashion, the dressing 10 provides a desired degree of lateral support to the outer edges of the nipple 6, such as occurring without application of any direct pressure to the reconstructed nipple, which is permitted to project through the rim 14 defined center aperture. Adherence of the device to the breast is further facilitated by the use of any tacky surfacing material (such as a gentle paper tape a portion of which is representatively designated at 13 in FIG. 3), as well as any compound or ingredient applied to a corresponding inner concave surface 16 of the body, this including a non-residue application of a material upon the inner surface 16 which provides a requisite degree of continual adhering support to the breast mound and areola. It is further envisioned that the molecular composition of the silicone material, combined with a desired texturing (or roughening) of the inner concave surface 16 and natural contact forces of adhesion generated by the body heat of the wearer, can to a large degree establish the requisite degree of holding forces between the device and the reconstructed breast mound, and without the need for separate adhesive materials.

The device 10 is constructed, as previously described in one preferred embodiment, of a medical grade silicone given its durable, cushioning and flexible nature, with its outer perimeter, dimensions, and variable thicknesses being largely dictated by the dimensions and contours of the reconstructed breast. As is further known, medical grade silicone is a material which is clinically proven to reduce scarring of tissue and is known to be sold in sheet from for such a purpose. This is particular value in the present application, given the existence of an incision scar associated with the breast reconstruction, the appearance of which is progressively minimized at a faster rate as a result of the application of the post surgical and reconstructive silicone dressing device.

Given this, it is desired that the silicone cushioned device can be customized (or produced in a wide range of varying shapes, sizes and configurations, to comfortably seat the reconstructed breast and nipple graft of the wearer. It is further envisioned and understood that other suitable materials, such as drawn from other types of polymeric and/or rubberized based materials can be substituted which provide similar cushioning to the breast and areola, with concurrent lateral and non-pressurized support to the wearer's reconstructed nipple.

Figure 4D:
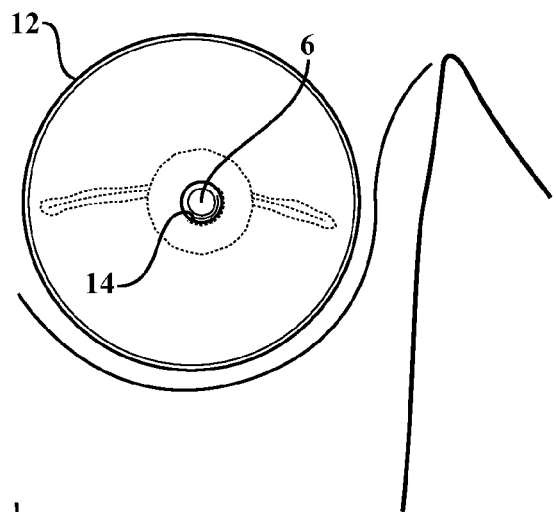
Figure 4E:
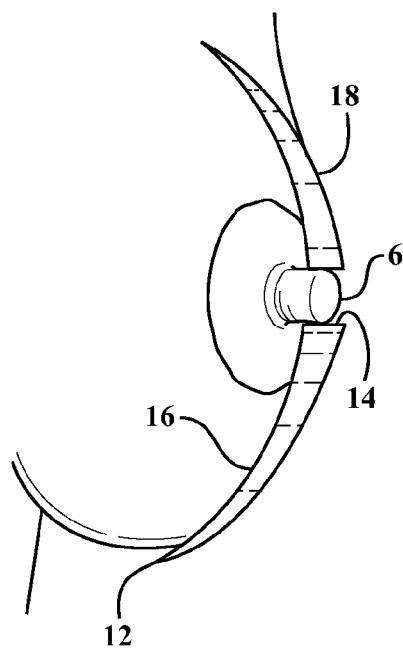
Figure 4F:
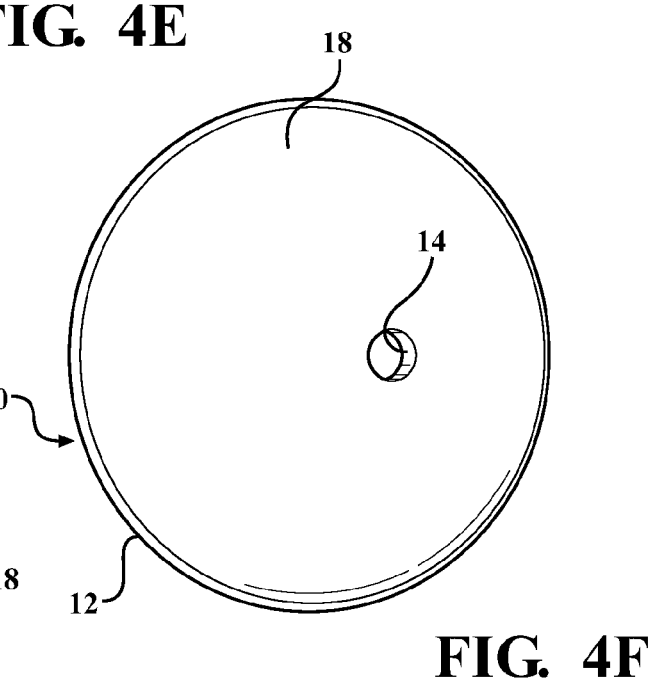
Figure 4G:
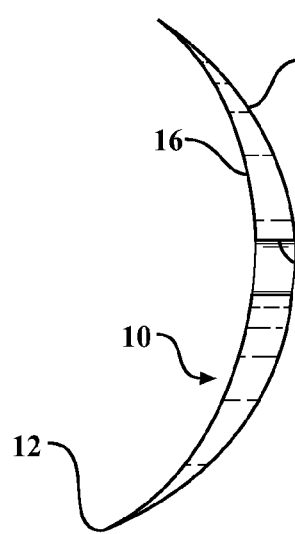

In use, the overall configuration of the device 10, combined with its generally gentle sloping convex outer surface 18 (opposite the inner concave surface 16 as shown in FIGS. 4E and 4F) provides a dressing which can be easily and invisibly concealed underneath a surgical bra or other garment and held in place by any disclosed adhesive (again such as a gentle paper tape as well as any other non-residue and tacky promoting application to the inner concave surface 16 as well as also possibly including a vacuum sealing aspect as will be subsequently described). Additional advantages of the device 10 include its wash-ability, as well of the central and aperture defined rim 14 facilitating evacuation of moisture or perspiration building up along the inside contact surface between the breast mound and areola and the inner concave surface 16 of the device.

Referring now to FIGS. 5A-5E, illustrated are a succession of views of the dressing in FIG. 4 and, with particular reference to the side views of FIGS. 5B-5E, better illustrates the range and variety of dressings which can be provided according to varying thicknesses and radii. In each instance, the sizing or scalability of the dressing body 10 increases progressively, with the inner nipple seating aperture concurrently incrementing from an original diameter 14 in FIG. 5B, to 14' in FIG. 5C, 14" in FIGS. 5D and 14'" in FIG. 5E. One variant of the invention further contemplates providing a plurality of bodies 10 of varying size and nipple aperture (this contemplated as including additional to consistent scalable sizes the inclusion of smaller sized bodies with larger aperture nipple seating locations and vice versa).

Figure 5A:
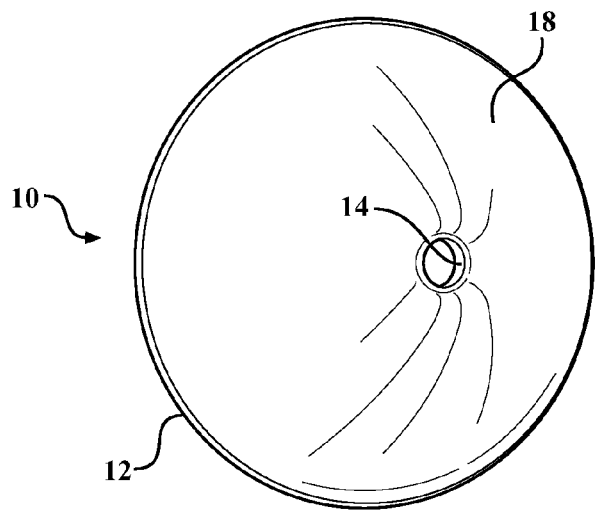
FIGS. 5A-5E illustrate a succession of views of the dressing in FIG. 4 and, with particular reference to the side views of FIGS. 5B-5E, the provision of dressings of varying thicknesses and radii.
Figure 5B:
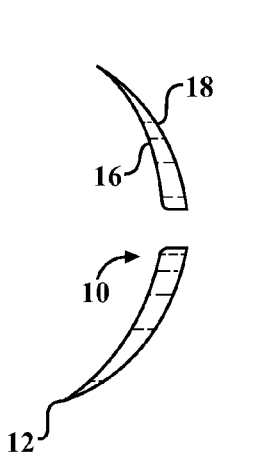
Figure 5C:
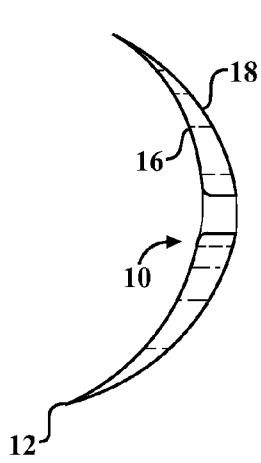
Figure 5D:
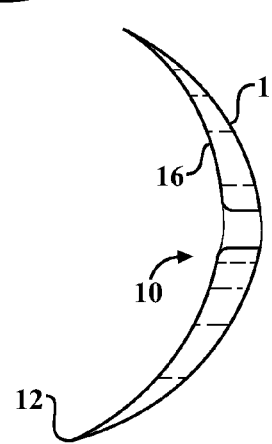
Figure 5E:
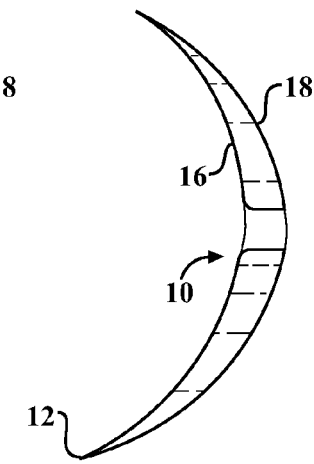
Figure 5F:
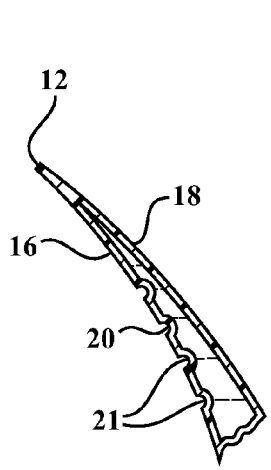
FIG. 5F is a partial perimeter edge view of a selected dressing and further showing an additional gripping pattern formed into the outer radial edge portion of the inner concave surface.

Proceeding to FIG. 5F, a partial perimeter edge view is shown of an inner perimeter surface extending and non-linear (or undulating) pattern, see concave depictions 20, of a selected dressing and which further illustrates an additional gripping pattern formed into the outer radial edge portion of the inner concave surface, this providing additional gripping (such as warmth induced gripping or other vacuum retaining)

support against the wearer's skin and about the outer perimeter of the dressing away form the central and nipple sensitive location.

The concave depictions 20, as well as any location along the smooth inner adhering surface 16 of the dressing, may also include any type of anti-infection or anti-microbial application, this including any form of chemical impregnation either formed into the body of the dressing or (as representatively depicted at 21) possible inlaid within the concave depressions in order to deliver anti-inflammatory or anti-infection compounds at the particular areas desired. It is also envisioned that the concave depictions 20 can be substituted by any other pattern, scheme or depiction calculated to enhance gripping aspects with or without the inclusion of other adhesive retention support.

Figure 6A:
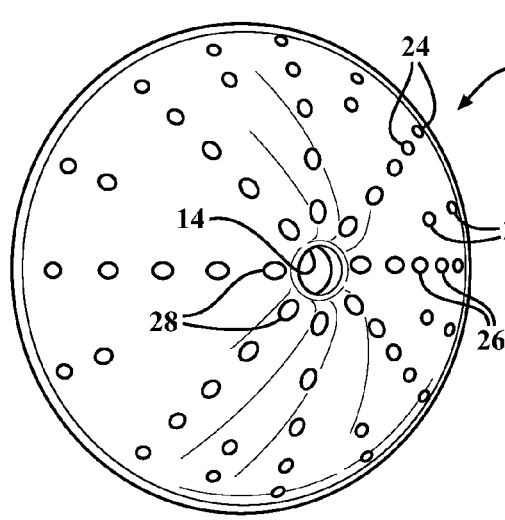
FIGS. 6A-D illustrate a further variant of reconstruction dressing incorporating a plurality of surface perforations to improve air permeability.
Figure 6B:
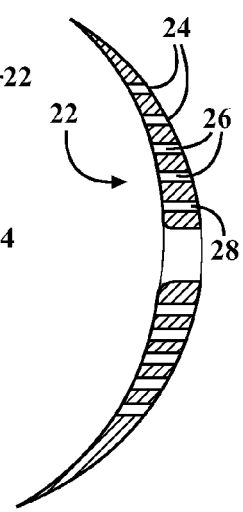

Referring now to FIGS. 6A-D, illustrated are further variants of a reconstruction dressing, see generally at 22 in each of the front and side cutaway views of FIGS. 6A and 6B, respectively. The dressing body 22 incorporates pluralities of surface perforations or apertures, at 24, 26, 28, et. seq. in a generally outermost to inner extending pattern formed through the surface of the dressing and in order to improve air permeability.

Figure 6C:
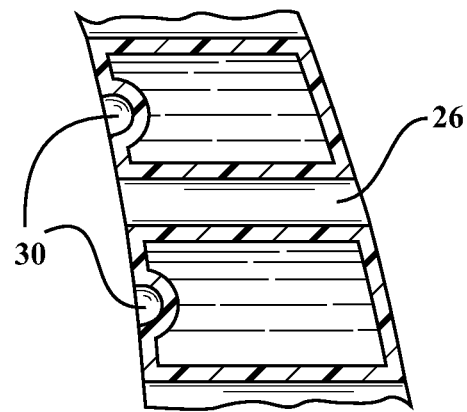
Figure 6D:
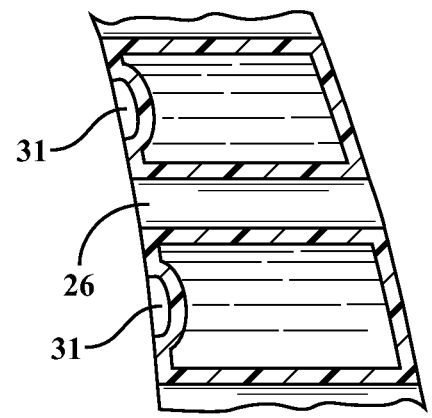

As further best shown in the enlarged partial cutaway views of FIGS. 6C and 6D (taken from FIG. 6B), illustrated are enlarged partial views of the pattern of the apertures is again shown, as is the formation of additional mini-concave pockets, see as depicted at 30 in a first pattern in FIG. 6C and which is similar to that depicted at 20 in FIG. 5F, and further at 31 in a second and non-limiting alternate pattern in FIG. 6D which is again defined along the interior concave surface of the dressing.

Figure 7A:
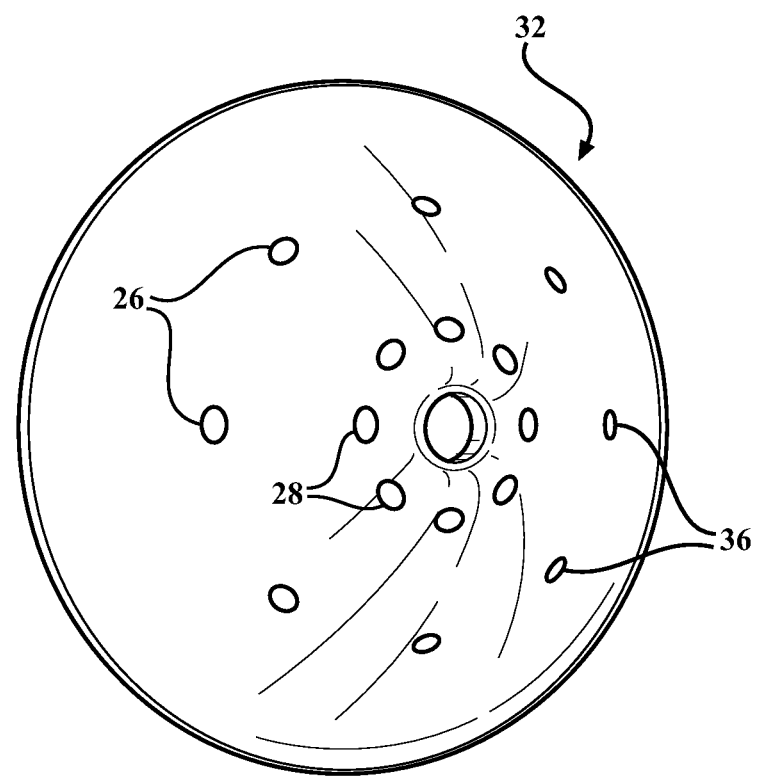
FIGS. 7A-7C illustrate a yet further variant of reconstruction dressing in which interiorly configured aperture patterns are combined with interior defined channels with outer baffles, and in order to facilitate ventilation of the wearer's skin.
Figure 7B:
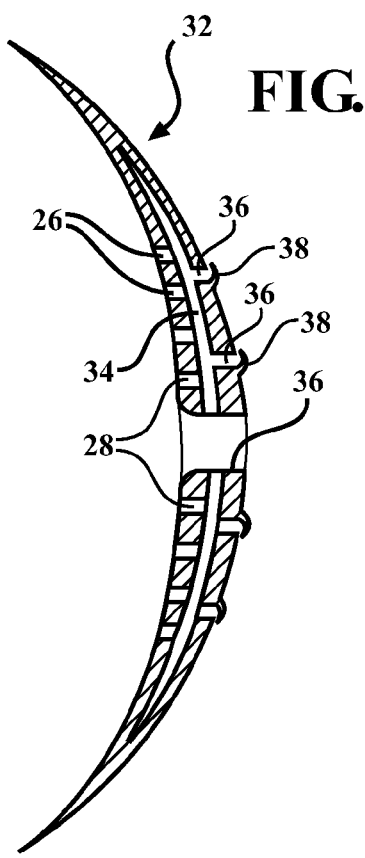
Figure 7C:
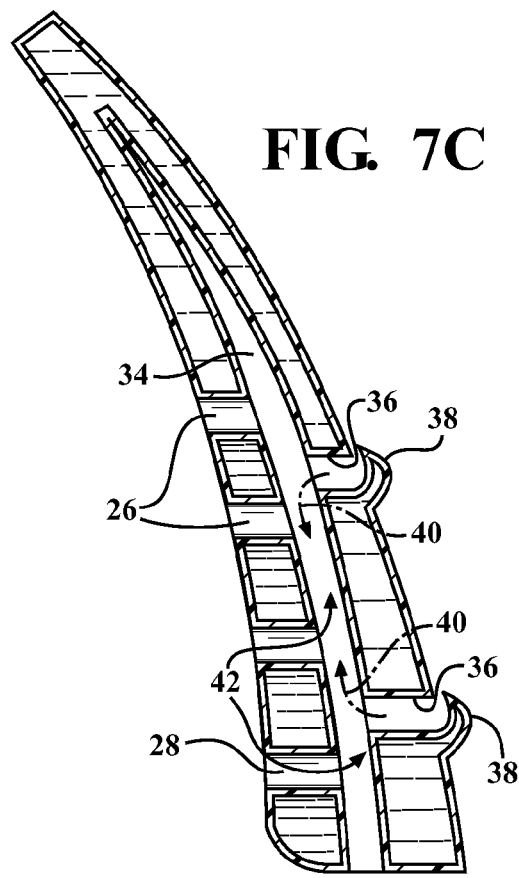

With reference to FIGS. 7A-7C, a series of perspective, side cutaway and enlarged partial cutaway illustrations are progressively shown of a yet further variant 32 of reconstruction dressing, and in which any desired pattern or arrangement of interiorly communicating apertures, such as selected from any combination of apertures and including those in positions as also depicted at 26 and 28 in FIG. 6A. As further shown in FIGS. 7B and 7C, the apertures 26 and 28 are internally communicated by channels 34, and which are in turn also communicated with outer baffles (including apertures 36 over which are positioned partially obstructing and projecting covering elements 38), this in order to facilitate a degree of controlled ventilation of the wearer's skin. In operation, the detail shown of the channel (FIG. 7C) allows fresh air to pass through the body (see directional arrows 40), while allowing the warmth of the body to escape (additional directional arrows 42). In this manner, it is envisioned that the skin surface of the wearer can be ventilated with a dressing incorporating the interior configured (e.g. molded) channels 34 and outer communicating baffle channels 36.

Figure 8:
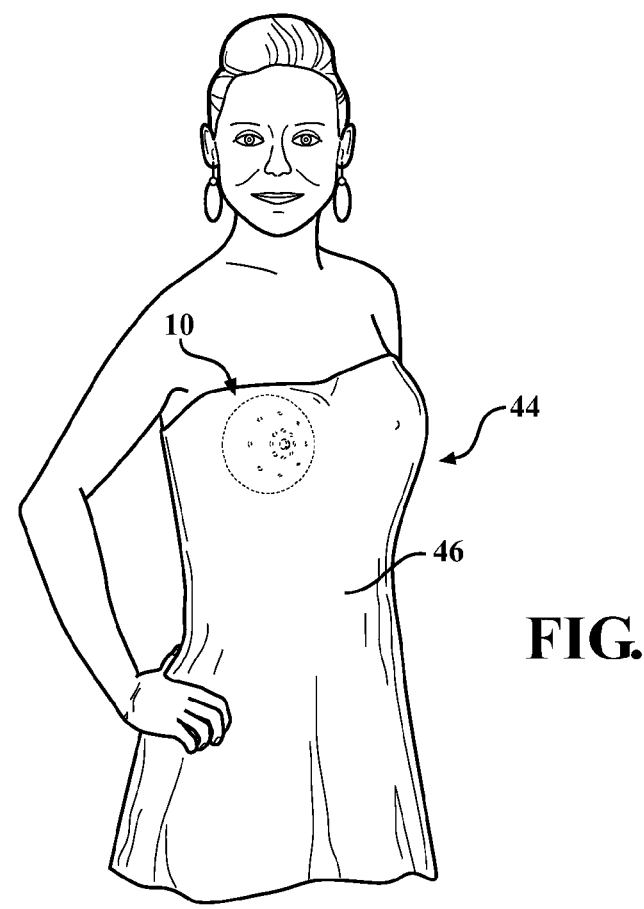
FIG. 8 is a use illustration in which the reconstruction dressing is worn invisibly underneath a dress, shirt or blouse.

Finally, FIG. 8 is a use illustration, generally at 44, in which the reconstruction dressing, such as previously shown at 10, is illustrated being worn invisibly underneath a dress 46, and which can be equally applicable to being worn underneath a shirt, blouse or any other female upper body garment. The ability to provide a contour establishing and invisible post operative dressing, suitably worn with existing clothing, has been found to be a desirable improvement over cumbersome prior art dressings.

Having described my invention, other and additional preferred embodiments will become apparent to those skilled in the art to which it pertains, and without deviating from the scope of the appended claims. This can include the use of any material composition within the dressing body, including again but not limited to medical grade silicone, as well as the construction or addition of any adhering, ventilating, medicating or supporting features to correspond and support the provision of the desirably dimensioned and laterally supporting central aperture for seating the reconstructed nipple therethrough.

We claim:

1. A dressing for post-operative use with a reconstructed a nipple associated with a breast mound, said dressing assisting in reducing scarring of tissue and comprising:

a flexible and one piece body constructed of a silicone material and having a three dimensional shape including a convex outer surface and a tacky concave inner surface such that said body is adapted for placement over and in adherence to the breast mound, said body further having an outer perimeter selected from any of including a rounded, oval or ellipsoidal shape, said body exhibiting a narrow most and tapered outer profile and increasing in dimension to a most thickened interior and so that said body is shaped to correspond to the contour of the female breast mound so as to be rendered substantially invisible when worn under an upper body garment; and an aperture defined by an inner rim configured within the most thickened interior of said body and adapted to seat therethrough the reconstructed nipple in a laterally supporting and non-pressure applied fashion.

2. The dressing as described in claim 1, further comprising a gripping pattern formed into the outer radial edge portion of an inner concave surface of said body and providing additional gripping support against the wearer's skin and about the outer perimeter of said dressing.

3. The dressing as described in claim 1, further comprising a plurality of ventilation perforations formed at spaced apart locations through said body and around said aperture defining inner rim.

4. The dressing as described in claim 1, said body further comprising interior molded channels communicating interior located apertures located proximate the wearer's skin with outer baffles for permitting fresh air to pass through said dressing to the breast and for generated body warmth to escape through said baffles.

* * * * *